US005246834A

United States Patent [19]

Tsuji et al.

[11] Patent Number: 5,246,834

[45] Date of Patent: Sep. 21, 1993

[54] ENZYME IMMUNOASSAY METHOD EMPLOYING ACETATE KINASE

[75] Inventors: Akio Tsuji; Masako Maeda, both of Tokyo; Motoo Nakajima, Noda, all of Japan

[73] Assignee: Kikkoman Corporation, Noda, Japan

[21] Appl. No.: 836,859

[22] Filed: Feb. 19, 1992

[30] Foreign Application Priority Data

Feb. 21, 1991 [JP] Japan .................................. 3-027588

[51] Int. Cl.[5] .............................................. C12Q 1/00

[52] U.S. Cl. .................................... 435/7.91; 435/7.9; 435/7.92; 435/7.93; 435/7.94; 435/7.95; 435/8; 435/15

[58] Field of Search .................... 435/7.92, 7.93, 7.94, 435/7.95, 8, 15, 29, 69.1, 69.8, 71.1, 170, 172.3, 183, 189, 194, 320.1, 822, 849; 43.6/518

[56] References Cited

U.S. PATENT DOCUMENTS 4,968,613 11/1990 Masuda et al. .................. 435/172.3

OTHER PUBLICATIONS

Fricke, et al. *J. Clin. Chem. Clin. Biochem.* V. 20 (1982) pp. 91-94.

European Search Report for European Application 92102840.3.

Shutenko, et al., "Adenylate kinase as a marker in immuno-enzyme analysis with a bioluminescence detection system," *Chemical Abstracts,* 110:244 (1989).

Yabuuchi et al., "Bioluminescence enzyme immunoassay of 17-α-hydroxyprogesterone using glucose dehydrogenase as label," Bunseki Kagaku, vol. 34 (1985) (English abstract included).

*Primary Examiner*—Sam Rosen

*Attorney, Agent, or Firm*—Banner, Birch, McKie & Beckett

[57] ABSTRACT

The present invention is intended to provide an EIA method utilizing bioluminescence using a firefly luciferase. The EIA method of the present invention is characterized by using an ATP-generating enzyme as a labeling enzyme, subjecting ATP generated to bioluminescence by the use of the firefly luciferase, and measuring the quantity of light emitted. Acetate kinase is a preferred enzyme used in the method.

4 Claims, 2 Drawing Sheets

ENZYME IMMUNOASSAY METHOD EMPLOYING ACETATE KINASE

BACKGROUND OF THE INVENTION

The present invention relates to an enzyme immunoassay method using an adenosine triphosphate (hereinafter referred to as "ATP")-generating enzyme as a labeling enzyme.

Analytical methods using chemiluminescence or bioluminescence are employed as methods for microanalysis of living body components. In particular, the quantum yield of luminous reactions utilizing the enzyme system of an organism is very high, and the luminous reactions are variously used in very highly sensitive analytical methods.

On the other hand, as to the application of luminous reactions to enzyme immunoassay (hereinafter referred to as "EIA"), chemiluminescence is mainly applied but several attempts have been made to apply bioluminescence to EIA. For example, there has been developed a method which comprises labeling an enzyme capable of generating a coenzyme which takes part in a luminous reaction, such as reduced form nicotinamide adenine dinucleotide, connecting the same to a bio-luminescence system, and thereby introducing bio-luminescence into EIA. This method is useful as a very highly sensitive EIA method because of the amplifying effect of the labeling enzyme. For example, it has been reported that an EIA method using glucose dehydrogenase as a labeling substance permits detection of $2.5\times10^{-12}$ g of 17-α-hydroxyprogesterone (Bunseki Kagaku, vol. 34 (1985), 6-10).

SUMMARY OF THE INVENTION

The present inventors aimed at bioluminescence using a firefly luciferase, as a means for measuring ATP with high sensitivity, and conducted various researches in order to apply the bioluminescence to EIA. Consequently, they have provided the present invention. That is, the present invention provides a method for enzyme immunoassay comprising using an ATP-generating enzyme as a labeling enzyme, subjecting ATP generated to bioluminescence by the use of the firefly luciferase, and measuring the quantity of light emitted.

DESCRIPTION OF PREFERRED EMBODIMENTS

Figure 1:
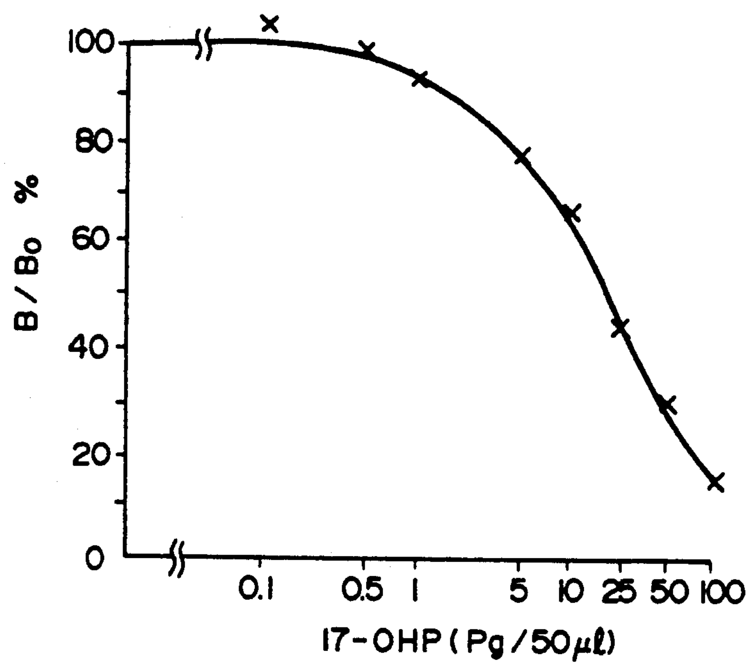
FIG. 1 shows a calibration curve for 17-60 -hydroxyprogesterone (17-OHP).

The EIA method of the present invention is characterized by using an ATP-generating enzyme as a labeling enzyme, subjecting ATP generated to bio-luminescence by the use of the firefly luciferase, and measuring the quantity of light emitted. The present invention is concretely explained below.

The present invention is characterized in that the ATP-generating enzyme is used as a labeling enzyme. In this invention, a known method for enzyme immunoreaction may be employed. As the known method, there can be exemplified a method comprising labeling a substance to be measured (antigen) with an enzyme, reacting the labeled substance with the corresponding antibody in competition with antigen in a sample, reacting the reaction product with a second antibody against the aforesaid antibody which has been previously immobilized on a solid phase, and then determining the amount of the enzyme on the solid phase (competitive method); and a method comprising reacting an antigen to be measured with the corresponding antibody previously immobilized on a solid phase, reacting the reaction product with enzyme-labeled antibody against the antigen, and then determining the amount of the enzyme on the solid phase (sandwich method). Conventional methods other than these methods may also be employed.

As the ATP-generating enzyme used as a labeling enzyme in the present invention, any enzyme may be used so long as it phosphorylates a substrate adenosine diphosphate (hereinafter referred to as "ADP") to generate ATP. The origin of the enzyme is not critical. Specific examples of the enzyme are acetate kinase, creatine kinase, pyruvate kinase, adenylate kinase, guanylate kinase, and guanidinoacetate kinase, etc. The labeling per se with the enzyme is carried out by a conventional method, for example, glutaraldehyde cross-linking method, periodic acid cross-linking method, maleimide crosslinking method, acid anhydride method and carbodiimide method [see "Koso Men-eki Sokuteiho" (published in 1982 by IGAKU-SHOIN LTD.), etc.]. Then, ADP is added as a substrate and reacted with the ATP-generating enzyme on a solid phase to generate ATP. The ATP is subjected to luminescence by the use of a firefly luciferase, and the quantity of light emitted is measured.

As the firefly luciferase used in this invention, there may be used any luciferase used for ATP measurement using a luciferin-luciferase system. There can be exemplified luciferases derived from Luciola cruciata, Luciola lateralis, Photinus pyralis, etc., and luciferases of these fireflies which are produced by genetic recombination.

The present invention provides an EIA method utilizing bioluminescence using the firefly luciferase, and permits highly sensitive measurement of various substances to be measured.

The present invention is more concretely illustrated below with reference to Examples.

EXAMPLE 1

Competitive immunoassay method of 17-α-hydroxyprogesterone (hereinafter referred to as "17-OHP") using acetate kinase (hereinafter referred to as "AK") as a labeling enzyme 1. Preparation of a 17-OHP-AK complex (1) Preparation of Reagents The following reagents (a) to (d) were prepared.

Reagent (a): a 17-OHP-3CMO solution

A 17-OHP-3CMO solution was prepared by dissolving a 17-α-hydroxyprogesterone-3-(0-carboxymethyl)oxime (available from Sigma Chemical Co.) in dioxane to a concentration of 0.1 M.

Reagent (b); an N-hydroxysuccinimide solution

An N-hydroxysuccinimide solution was prepared by dissolving an N-hydroxysuccinimide in dioxane to a concentration of 0.14 M.

Reagent (c): a DCC solution

A DCC solution was prepared by dissolving a dicyclohexylcarbodiimide in dioxane to a concentration of 0.14 M.

Reagent (d): an AK solution

An AK solution was prepared by dissolving an acetate kinase (available from Unitika Ltd.) in 50 mM phosphate buffer (pH 7.4) to a concentration of 1.16 mg/ml.

(2) Labeling reaction (carbodiimide method)

Reagents (a), (b) and (c) were mixed in amounts of 1 ml, 0.5 ml and 0.5 ml, respectively, and the reaction was carried out at room temperature for 3 hours. The insoluble materials were centrifugally removed, after which the residue was added to 0.25 ml of reagent (d), and the reaction was carried out overnight at 4° C. The reaction solution was dialyzed against 50 mM Trishydrochloric acid buffer (pH 7.4) and the dialyzed solution was centrifuged (at 2,500 r.p.m. for 10 minutes). The supernatant was purified by gel filtration using Toyo Pearl HW-55 (mfd. by Tosoh Ltd.) to prepare a 17-OHP-AK complex.

2. Measurement of 17-OHP (1) Preparation of Reagents

The following reagents (a) to (f) were prepared.

Reagent (a): Anti-17-OHP Antiserum

The antiserum was prepared by immunizing a rabbit with an antigen 17-α-hydroxyprogesterone-3-(0-carboxymethyl)oxime-BSA (available from Sigma Chemical Co) according to a conventional method. It was used after proper dilution.

Reagent (b): a 17-OHP-AK Complex Solution

A 17-OHP-AK complex solution was prepared by diluting the 17-OHP-AK complex prepared in the above item 1, in 200 times with 50 μl of 50 mM Tris-hydrochloric acid buffer (pH 7.4).

Reagents (c): 17-OHP Solutions

17-OHP solutions were prepared by dissolving 0.1 to 200 pg of 17α-hydroxyprogesterone (available from Sigma Chemical Co.) in 50 μl of 50 mM Tris-hydrochloric acid buffer (pH 7.4).

Reagent (d): a substrate solution

A substrate solution was prepared by dissolving ADP, acetylphosphoric acid and magnesium acetate in 50 mM Tris-hydrochloric acid buffer (pH 7.4) to adjust their concentrations to 10 μM, 1 mM and 30 mM, respectively. Reagent (e): a buffer solution for measurement A buffer solution for measurement was prepared by dissolving magnesium acetate and a blocking agent for immunological experiment (Blockace TM, mfd. by Dai Nippon Pharmaceutical Co.) in 50 mM Tris-hydrochloric acid buffer (pH 7.4) to adjust their concentrations to 30 mM and 10%, respectively.

Reagent (f): a luminous reagent solution

A luminous reagent solution was prepared by dissolving a vial of a luminous reagent of a kit for measuring ATP (Lucifer-LU TM, mfd. by Kikkoman Corporation) in a vial of a liquid for dissolving the luminous reagent.

(2) Measurement

After 50 μl of reagent (a), 50 μl of reagent (b) and 50 μl of reagent (c) were added in a test tube containing goat anti-rabbit IgG antibody immobilized on the inner surface of the test tube which had been prepared by a conventional method, the reaction was carried out overnight at 4° C. The inside of the test tube was washed three times with 50 mM Tris-hydrochloric acid buffer (pH 7.4), and the washings were removed. Thereafter, 50 μl of reagent (d) and 100 μl of reagent (e) were added in the test tube, and the reaction was carried out at 37° C. for 1 hour. In the test tube was then added 100 μl of reagent (f), and the light emitted was integrated for 15 seconds by means of a luminometer (LUMINESCENCE READER BLR-201 TM, mfd. by ALOKA CO., LTD.). The results obtained are shown in FIG. 1. From FIG. 1, it can be seen that at least $0.5\times10^{-12}$ g of 17-OHP can be detected.

EXAMPLE 2

Sandwich Immunoassay Method of Thyroid-Stimulating Hormone (TSH) Using AK as a Labeling Enzyme 1. Preparation of Mouse Anti-Fab'-AK (AK-Labeled Fab')

(1) Preparation of reagents

The following reagents (a) to (e) were prepared.

Reagent (a): acetate buffer saline (ABS)

ABS was prepared by dissolving sodium chloride in 0.1 M acetate buffer (pH 4.5) to a concentration of 0.9%.

Reagent (b): phosphate buffer saline (PBS)

PBS was prepared by dissolving sodium chloride in 0.1 M phosphate buffer (pH 7.0) to a concentration of 0.9%.

Reagent (c): A Reagent Solution for Reduction Reaction

A reagent solution for reduction reaction was prepared by dissolving 2-mercaptoethanol and EDTA in reagent (b) to adjust their concentrations to 0.1 M and 5 mM, respectively.

Reagent (d): an AK solution

An AK solution was prepared by dissolving 0.66 mg of AK (available from Unitika Ltd.) in 1 ml of reagent (b).

Reagent (e): a reagent solution for modification with maleimid

A reagent solution for modification with maleimide was prepared by dissolving 5 mg of N-(ε-maleimidocaproyloxyl)succinimide (mfd. by Dojin Kagaku) in 1 ml of dimethylformamide.

(2) Labeling Reaction (Maleimide Method)

After 2 ml of mouse anti-TSH IgG (available from Tosoh Ltd.) (7 mg/ml) was dialyzed overnight against reagent (a), the dialyzed solution was concentrated by ultrafiltration. To the concentrate was added 0.28 mg of pepsin, and the reaction was carried out overnight at 37° C. Thereafter, $F(ab')_2$ was separated from the reaction solution by gel filtration. The $F(ab')_2$ was concentrated and then mixed with 50 μl of reagent solution (c), and the reaction was carried out at 37° C. for 90 minutes. Then, Fab, was separated from the reaction solution by gel filtration. On the other hand, 8.4 μl of reagent (e) was added to 1 ml of reagent (d), and the reaction was carried out at 37° C. for 90 minutes. The reaction product (maleimide-modified AK) was separated by gel filtration. This reaction product was mixed with the Fab' obtained in the above, and the reaction was carried out at 3020 C. for 2 hours. Thereafter, a mouse anti-TSH Fab,-AK complex (AK-labeled Fab,) was obtained from the reaction mixture by gel filtration.

2. Determination of TSH (1) Preparation of Reagents

The following reagents (a) to (f) were prepared.

Reagent (a): HEPES-Blockace

HEPES-Blockace TM was prepared by adding Blockace (mfd. by Dai Nippon Pharmaceutical Co.) to 50 mM HEPES buffer (pH 7.0) to adjust its concentration to 10%.

Reagents (b): TSH Solutions

TSH solutions having a concentration of 0.001 to 10 μIU/ml were prepared by diluting TSH (available from Tosoh Ltd.) with reagent (a).

Reagent (c): A Buffer Solution for Measurement

A buffer solution for measurement was prepared by dissolving magnesium chloride and Blockace (mfd. by Dai Nippon Pharmaceutical Co,) in 50 mM HEPES buffer (pH 7.0) to adjust their concentrations to 30 mM and 10%, respectively.

Reagent (d): An AK-Labeled Fab, Solution

An AK-labeled Fab, solution was prepared by diluting the mouse anti-TSH Fab'-AK complex (AK-labeled Fab') prepared in the above item 1, in 5,000 times with reagent (a).

Reagent (e): A Substrate Solution

A substrate solution was prepared by dissolving ADP and acetylphosphoric acid in reagent (c) to adjust their concentrations to 5 μM and 2.5 mM, respectively.

Reagent (f): a luminous reagent

A luminous reagent solution was prepared by dissolving a vial of a luminous reagent of a kit for measuring ATP (Lucifer-LU TM, mfd. by Kikkoman Corporation) in a vial of a liquid for dissolving the luminous reagent.

Reagent (g): A Washing Solution

A washing solution was prepared by adding Tween 20 TM (mfd. by Wako Pure Chemical Industries, Ltd.) to reagent (a) to adjust its concentration to 0.02%.

(2) Measurement

To a micro-titer plate (mfd. by Nunc) having mouse anti-TSH IgG immobilized thereon which had been prepared by a conventional method was added 100 μl of reagent (b), and the reaction was carried out at 37° C. for 1 hour. The plate was washed three times with reagent (g) and the washings were removed, after which 100 μl of reagent (d) was added to the residue and the reaction was carried out at 37° C. for 1 hour. The plate was washed three times with reagent (g) and the washings were removed, after which 100 μl of reagent (e) was added to the residue and the reaction was carried out at 37° C. for hour. Then, 95 μl of the reaction solution was transferred to a test tube, and 100 μl of reagent (f) was added. The light thus emitted was integrated for 20 seconds by means of a luminometer (LUMINESCENCE READER BLR-201 TM, by ALOKA CO., LTD.). The results obtained are shown in FIG. 2.

Figure 2:
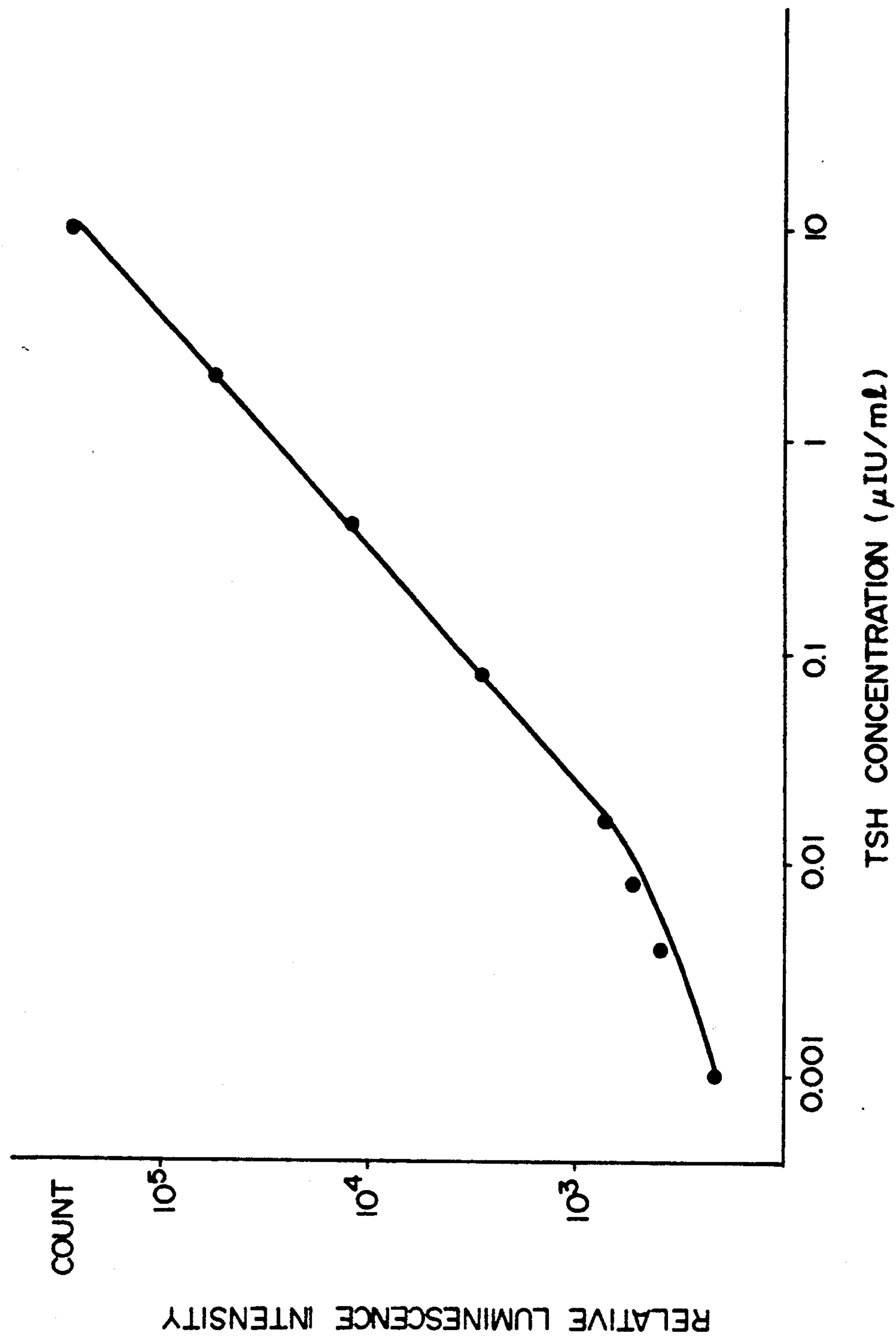
FIG. 2 shows a calibration curve for thyroidstimulating hormone (TSH).

From FIG. 2, it can be seen that TSH in a quantity lower than 0.01 μIU/ml may be detected.

EXAMPLE 3

Sandwich Immunoassay Method of Immunoglobulin G (IgG) Using AK as a Labeling Enzyme 1. Preparation of a Goat Anti-Rabbit IgG-AK Complex (AK-Labeled Fab')

(1) Preparation of Reagents

The following reagents (a) to (e) were prepared.

Reagent (a): ABS

ABS was prepared by dissolving sodium chloride in 0.1 M acetate buffer (pH 4.5) to a concentration of 0.9%.

Reagent (b): PBS

PBS was prepared by dissolving sodium chloride in 100 mM phosphate buffer (pH 7.0) to a concentration of 0.9%.

Reagent (c): A Reagent Solution for Reduction Reaction

A reagent solution for reduction reaction was prepared by dissolving 2-mercaptoethanol and EDTA in reagent (b) to adjust their concentrations to 0.1 M and 5 mM, respectively.

Reagent (d): An AK Solution

An AK solution was prepared by dissolving 0.66 mg of AK (available from Unitika Ltd.) in 1 ml of reagent (b).

Reagent (e): A Reagent Solution for Modification with Maleimide

A reagent solution for modification with maleimide was prepared by dissolving 5 mg of N-(ε-meleimidocaproyloxyl)succinimide (mfd. by Dojin Kagaku) in 1 ml of dimethylformamide.

(2) Labeling Reaction (Maleimide Method)

After 2 ml of goat anti-rabbit IgG (available from Seikagaku Kogyo Corporation) (7 mg/ml) was dialyzed overnight against reagent (a), the dialyzed solution was concentrated by ultrafiltration. To the concentrate was added 0.28 mg of pepsin, and the reaction was carried out overnight at 37° C. Thereafter, $F(ab')_2$ was separated from the reaction solution by gel filtration. The $F(ab')_2$ was concentrated and then mixed with 50 μl of reagent (c), and the reaction was carried out at 37° C. for 90 minutes. Then, Fab, was separated from the reaction solution by gel filtration. On the other hand, 8.4 μl of reagent (e) was added to 1 ml of reagent (d), and the reaction was carried out at 37° C. for 90 minutes. The reaction product (maleimide-modified AK) was separated by gel filtration. The reaction product was mixed with the Fab' obtained in the above, and the reaction was carried out at 30° C. for 2 hours. Thereafter, a goat anti-rabbit IgG-AK complex (AK-labeled Fab') was obtained from the reaction mixture by gel filtration.

2. Determination of Rabbit IgG (1) Preparation of Reagents

The following reagents (a) to (f) were prepared.

Reagent (a): PBS-BSA

PBS-BSA was prepared by dissolving sodium chloride and bovine serum albumin (BSA) in 100 mM phosphate buffer (pH 7.0) to adjust their concentrations to 0.9% and 0.1%, respectively.

Reagents (b): Rabbit IgG Solutions

Rabbit IgG solutions having a concentration of 0.25 to 250 ng/ml were prepared by diluting rabbit IgG (available from Seikagaku Corporation) with reagent (a).

Reagent (c): A Buffer Solution for Measurement

A buffer solution for measurement was prepared by dissolving magnesium acetate and Blockace (mfd. by Dai Nippon Pharmaceutical Co.) in 50 mM Tris-hydrochloric acid buffer (pH 7.4) to adjust their concentrations to 30 mM and 10%, respectively.

Reagent (d): an AK-labeled Fab' Solution

An AK-labeled Fab' solution was prepared by diluting the goat anti-rabbit IgG-AK complex (AK-labeled Fab,) prepared in the above item 1, in 1,000 times with reagent (a).

Reagent (e): a substrate solution

A substrate solution was prepared by dissolving ADP and acetylphosphoric acid in 50 mM Tris-hydrochloric acid buffer (pH 7.4) to adjust their concentrations to 10 μm and 1 mM, respectively.

Reagent (f): A Luminous Reagent Solution

A luminous reagent solution was prepared by dissolving a vial of a luminous reagent of a kit for measuring ATP (Lucifer-LU, mfd. by Kikkoman Corporation) in a vial of a liquid for dissolving the luminous reagent.

(2) Measurement

After 100 μl of reagent (b) was added in a test tube containing goat anti-rabbit IgG antibody immobilized on the inner surface of the test tube which had been prepared by a conventional method, the reaction was carried out at 37° C. for 1 hour. The inside of the test tube was washed three times with reagent (c), and the washings were removed. Then, 100 μl of reagent (d) was added in the test tube, and the reaction was carried out at 37° C. for 1 hour. The inside of the test tube was washed three times with reagent (c), and the washings were removed. Thereafter, 50 μl each of reagent (c) and reagent (e) were placed in the test tube, and the reaction was carried out at 37° C. for 1 hour. Subsequently, 100 μl of reagent (f) was placed in the test tube, and the light thus emitted was integrated for 15 seconds by means of a luminometer (LUMINESCENCE READER BLR-201 TM, mfd. by ALOKA CO., LTD.). The results obtained are shown in FIG. 3.

Figure 3:
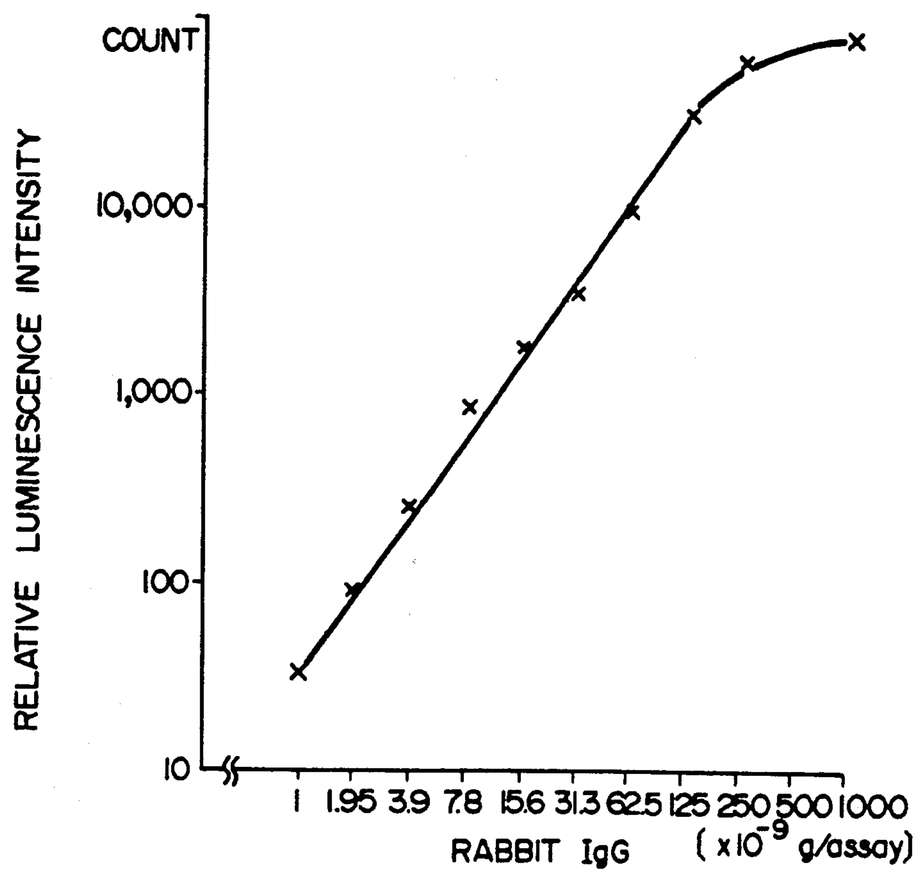
FIG. 3 shows a calibration curve for rabbit IgG.

From FIG. 3, it can been seen that $1\times10^{-9}$ g/assay of rabbit IgG may be detected.

What is claimed is:

1. A method for enzyme immunoassay of a substance to be measured (analytic), comprising:

cross-linking acetate kinase to the analyte to label said analyte, and determining the amount of analyte by:

adding adenosine disphosphate to said analyte-linked acetate kinase to generate adenosine triphosphate, and measuring the adenosine triphosphate generated using a bioluminescence reaction in which a firefly luciferase is employed and the quantity of light emitted is measured.

2. A method according to claim 1, wherein the firefly luciferase is one member selected from the group consisting of firefly luciferases derived from Luciola cruciata, Luciola lateralis and Photinus pyralis, respectively.

3. A method according to claim 1, wherein the firefly luciferase is one produced by genetic recombination.

4. A method according to claim 1, wherein the enzyme immunoassay is carried out by a competitive method or a sandwich method.

* * * * *